United States Patent [19]

Kennedy et al.

[11] Patent Number: 5,376,373
[45] Date of Patent: Dec. 27, 1994

[54] METHOD OF INHIBITING RADIATION INDUCED WEIGHT AND HAIR LOSS

[75] Inventors: Ann R. Kennedy, Wynnewood, Pa.; Bernard F. Szuhaj, Fort Wayne, Ind.

[73] Assignees: Trustees of the University of Pennsylvania, Philadelphia, Pa.; Central Soya Co., Inc., Fort Wayne, Ind.

[21] Appl. No.: 29,472

[22] Filed: Mar. 11, 1993

Related U.S. Application Data

[63] Continuation-in-part of Ser. No. 973,335, Nov. 2, 1992, Pat. No. 5,338,547, which is a continuation-in-part of Ser. No. 824,719, Jan. 17, 1992, Pat. No. 5,217,717, which is a continuation of Ser. No. 579,155, Sep. 6, 1990, abandoned.

[51] Int. Cl.$^5$ .............................................. A61K 35/78
[52] U.S. Cl. .................... 424/195.1; 514/738
[58] Field of Search ....................... 424/195.1; 514/738

[56] References Cited

U.S. PATENT DOCUMENTS

| | | | |
|---|---|---|---|
| 3,365,440 | 1/1968 | Circle et al. | 260/123.5 |
| 4,793,996 | 12/1988 | Kennedy et al. | 424/195.1 |
| 5,217,717 | 6/1993 | Kennedy et al. | 424/195.1 |

OTHER PUBLICATIONS

Kim, J. et al., *Seminars in Oncology* 10:86–92, 1983.
Verhey, L. J. and Sedlacek, R., "Determination of the Radioprotective Effects of Topical Applications of MEA, WR–2721, and N–acetylcysteine on Murine Skin," *Rad. Res.* 93:175–183, 1983.
Potera, M. E. et al., "Prophylaxis of Radiation Dermatitis with a Topical Cortisone Cream," *Radiology* 143:775–777, 1982.
Ohlsen, L. et al., "Local Anaesthetics Modifying the Dermal Response of Irradiation," *Acta Oncological* 26:467–476, 1987.
Berenblum et al., "Inhibition of Radiation-Induced Lymphatic Leukemia in C57BL Mice by 19S Alpha-2-Globulin ($\alpha_2$—MG) From Human Blood Serum," *Radiation Research* 60:501–505, 1974.
Liebner, E. J. et al., "Lowering the Skin Temperature of the Irradiated Field," *Am. J. Roent. Rad. Ther and Nucl. Med.* 88:976–987, 1962.

*Primary Examiner*—John W. Rollins
*Assistant Examiner*—Howard C. Lee
*Attorney, Agent, or Firm*—Jane Massey Licata

[57] ABSTRACT

Methods for inhibiting radiation induced weight and hair loss are provided. A Bowman Birk Inhibitor product is administered in an effective amount, preferably orally, to inhibit cutaneous manifestations of radiation and weight loss.

11 Claims, 2 Drawing Sheets

METHOD OF INHIBITING RADIATION INDUCED WEIGHT AND HAIR LOSS

INTRODUCTION

This application is a continuation-in-part of Ser. No. 973,335, filed Nov. 2, 1992, now U.S. Pat. No. 5,338,547 which was a continuation-in-part of Ser. No. 824,719 filed Jan. 17, 1992, now U.S. Pat. No. 5,217,717 which was a continuation of Ser. No. 579,155, filed Sep. 6, 1990, now abandoned.

FIELD OF THE INVENTION

This invention relates to methods of inhibiting radiation induced weight and hair loss by administration of a Bowman-Birk Inhibitor (BBI) product.

BACKGROUND OF THE INVENTION

Radiation induced weight and hair loss are clinical, cosmetic and psychological problems for cancer patients. Hair loss in patients receiving radiation therapy for cranial and extracranial lesions may have major psycho-social consequences for the patient. Where hair loss is due to direct radiation, it is usually irreversible. Attempts to minimize radiation dermatitis and hair loss have been directed at using topical radiation protectant agents (Kim, J. et al., Seminars in Oncology 1983, 10, 86–92; Verhey, L J and Sedlacek, R., Rad. Res. 1983, 93, 175–183); lowering skin temperature in the radiation field (Liebner, E J et al., Am. J. Roent. Rad. Ther and Nucl. Med. 1962, 88, 976–987); applying topical cortisone (Potera, M E et al., Radiology 1982, 143, 775–777); and use of local anesthetics (Ohlsen, L. et al., Acta Oncological 1987, 26, 467–476). The success of these therapies has been minimal and none are in common clinical usage.

Weight loss is a well recognized problem in cancer patients treated with radiation and/or cancer chemotherapeutic agents, and has been shown to be an independent prognostic indicator of decreased survival rates. The cause of this weight loss is believed to be related to both decreased caloric intake/absorption and increased energy requirements. However, it has been found that increased caloric intake has not improved survival for patients with a variety of advanced cancers. Thus, the prevention of weight loss should be considered as an important goal to decrease morbidity and mortality associated with cancer-related therapies.

U.S. Pat. 4,793,996 (Kennedy et al.) discloses a process comprising treating soybeans with acetone, followed by ethanol extraction and acetone precipitation for obtaining Bowman Birk Inhibitor (BBI). The soybeans may be defatted prior to acetone treatment. In addition, BBI may be further purified by conventional techniques. Kennedy et al. discovered that in the conventional process for preparing BBI from soybeans, a factor remained which adversely affected the ability of BBI to inhibit the malignant transformation of cells. If the factor was removed, the resulting BBI product was capable of inhibiting the malignant transformation of cells. It was found to be possible to remove this factor by treating the soybeans with acetone prior to the ethanol extraction step.

Kennedy et al., in U.S. application Ser. No. 824,719 filed Jan. 17, 1992 now U.S. Pat. No. 5,217,717 entitled "Methods of Making Soybean Bowman-Birk Inhibitor Concentrate and Use of Same As a Human Cancer Preventative and Therapy", which is incorporated herein in its entirety, describe methods for producing novel BBI concentrate products. Those BBI concentrate products are employed by the methods of the present invention. The process described to produce those BBI products was found to be economically superior due to the avoidance of an aqueous alcohol extraction step and the use, in certain embodiments, of ultrafiltration as a separation process step.

SUMMARY OF THE INVENTION

Methods for inhibiting radiation induced weight and hair loss by administration of a Bowman Birk Inhibitor product are provided. It has been found that hair and weight loss are minimized following dietary supplementation with a Bowman-Birk Inhibitor product.

The methods described by the present invention may employ the use of a BBI product produced in accordance with the following methods. The source material for preparing the BBI products is soybean solubles. The soybean solubles are preferably obtained from soybean flakes or soy flour. The soybean flakes or soy flour are first subjected to a hexane defatting step. The defatted material is subjected to an acidic aqueous extraction step, pH from about 4 to 5, and the insolubles are removed to produce the soybean solubles. The process for the production of soybean solubles are well known in the art as shown by U.S. Pat. No. 3,365,440, which is incorporated herein in its entirety. The soybean solubles are conventionally produced at a relatively high solids concentration, usually at a solids concentration of at least about 50 percent by weight as recognized by the Association of American Feed Control Officials Incorporated.

The BBI product is produced by diluting the soybean solubles with water, preferably to about 15-25% by weight solids content, followed by centrifugation to produce purified soybean solubles. The purified solubles are then diluted with water, preferably to about 10-12% by weight solids, to produce reslurried purified soybean solubles. The reslurried solubles are then subjected to ultrafiltration to produce a crude BBI concentrate. The crude concentrate is then diluted with water and spray dried to produce the Bowman Birk Inhibitor Concentrate (BBIC) product. In another process embodiment for the production of the BBIC product, the diluted crude BBI concentrate is subjected to another ultrafiltration step to produce a semi-crude BBI concentrate which is then spray dried to produce the BBIC product.

In a preferred process embodiment, the semi-crude BBI concentrate is treated with acetone to produce a BBI concentrate precipitate. After settling and decanting the resulting purified BBI concentrate precipitate is air dried, ground, reslurried with water, filtered and then lyophilized or spray dried to produce the BBIC product.

The BBIC product can be produced in accordance with another process embodiment wherein the time-consuming step(s) are eliminated by starting with soy solubles and applying the acetone treatment to a substrate that has a substantially higher concentration of BBI than that in the defatted soy flour/flake of the prior art, resulting in a more economical process for production.

It was surprising found that a Bowman-Birk Inhibitor product inhibited radiation induced weight and hair loss.

DETAILED DESCRIPTION OF THE INVENTION

Figure 1A:
FIGS. 1(a) and 1(b) are photographs of irradiated C57BL mice. The mouse in FIG. 1(a) received a Bowman-Birk Inhibitor dietary supplement. The mouse in FIG. 1(b) did not. Extensive hair loss was observed in mice that did not receive BBI dietary supplementation; an example of such a mouse is shown in FIG. 1(b).

The present invention concerns methods of inhibiting radiation induced weight and hair loss by administration of a Bowman-Birk Inhibitor product. The Bowman-Birk product may be produced in accordance with the methods described herein. The administration can be by any acceptable and convenient mode, with oral administration preferred.

The preparation of the BBI product useful in the methods of the present invention includes the steps of (1) providing soybean solubles produced from acidic aqueous-extracted hexane-defatted soybeans in the absence of an ethanol extraction step, the soybean solubles preferably having a solids concentration of at least about 50 percent by weight; (2) diluting the soybean solubles with an aqueous solution to form a slurry, preferably a 15 to 20 percent by weight solid solution; (3) separating the aqueous soluble portion of the soybean solubles from the slurry to form a purified soybean soluble composition; (4) diluting the purified soybean soluble composition with an aqueous solution, preferably to about a 10–12% solid solution, and ultrafiltering the aqueous soluble portion of the diluted purified soybean soluble composition at least once, retaining the supernatant fluid, to form a crude BBI concentrate; and (5) drying the crude BBI concentrate, preferably by spray drying, and recovering the BBIC product. The process can include an optional, additional dilution of the crude BBI concentrate with an aqueous solution followed by an ultrafiltration step to form a semi-crude BBI concentrate prior to the drying step. The process can be further modified by diluting the semi-crude BBI concentrate with acetone and retaining the precipitated acetone insoluble portion prior to the drying step.

In accordance with one embodiment of the process to produce the BBI product, soybean solubles are diluted with water to 18% solids and then centrifuged to produce purified soybean solubles. The purified solubles are diluted with water to 8% solids to produce reslurried purified soybean solubles which are subjected to ultrafiltration (10,000 m.w. membrane). The resulting crude BBI concentrate is diluted with water (1:1) and then subjected to a second ultrafiltration step (1,000 m.w. membrane) to produce a semi-crude BBI concentrate. The semi-crude concentrate is treated with acetone (2.2:1) to produce a BBI concentrate precipitate. After settling and decanting, the resulting purified BBI concentrate precipitate is air dried, ground, reslurried with water to 15% solids, filtered (Buchner funnel/Whatman #1) and then lyophilized to produce the BBIC product.

In another embodiment of the process to produce the BBIC product, purified soybean solubles are produced as described above and then diluted to 10% solids. The resulting reslurried purified soybean solubles are then treated as described in the foregoing to produce a semi-crude BBI concentrate which is treated with acetone (1.66 to 1) to produce a BBI concentrate precipitate. The BBIC product is produced as described above, with the exception that the filtered precipitate is spray dried rather than lyophilized.

In still another embodiment of the process to produce the BBIC product, soybean solubles are diluted with water to 15–20% solids and centrifuged to produce purified soybean solubles. The purified solubles are diluted with water to 10% solids to produce reslurried purified soybean solubles which are subjected to ultrafiltration (1,000 m.w. membrane). The resulting crude BBI concentrate is diluted with water (1:1) and spray dried to produce the BBIC product.

In yet another embodiment of the process to produce the BBIC product, soybean solubles are diluted with water to 16% solids and centrifuged to produce purified soybean solubles. The purified solubles are diluted with water to 10% solids. The resulting reslurried purified solubles are then subjected to ultrafiltration (10,000 m.w. membrane), producing a crude BBI concentrate. The crude concentrate is diluted with water (1:1) and again subjected to ultrafiltration (1,000 m.w. membrane) to produce a semicrude BBI concentrate which is spray dried to produce the BBIC product.

In another embodiment of the process to produce the BBIC product, the ultrafiltration step(s) are eliminated by starting with soy solubles, and applying the acetone treatment to a substrate that has a substantially higher concentration of BBI than that in defatted soy flour/flake. In this process, insolubles are removed from acid aqueous-extracted hexane defatted soybeans to produce soybean solubles having a solids content of at least 50%. The soybean solubles are diluted with water to a solids concentration of from about 15–20% and are then centrifuged to produce purified soybean solubles. Acetone is added to the supernatant to produce a crude BBI concentrate precipitate, which is allowed to settle. The resulting precipitate containing the partially purified BBI is then resuspended in water and centrifuged. Acetone is then added to the supernatant and the resulting water soluble, acetone insoluble precipitate allowed to settle, and then dried to produce the BBIC product. An optional additional acetone resuspension step can be employed before the final drying step.

The BBIC products made in accordance with the various processes set forth herein are useful for inhibiting radiation induced weight and hair loss. These Bowman-Birk Inhibitor products may be administered either alone or in combination with a pharmaceutically acceptable carrier. Oral administration, either as a dietary supplement or a pharmaceutical composition are contemplated by the teachings of this invention.

In studies with C57BL mice absence of hair loss, overall shiny coats and decreased weight loss were unexpectedly found when their diet was supplemented with a Bowman-Birk concentrate product.

Figure 1B:

Radiation induced leukemia in C57BL mice is an established animal carcinogenesis assay system. See, for example, (Berenblum et al., *Radiation Research* 1974, 60, 501–505). Although the Bowman-Birk Inhibitor (BBI) product did not affect the incidence of cancer in this study, three unexpected findings were noted. At the time of death due to leukemia (approximately 80% of both the BBI supplemented and non-BBI supplemented mice died of leukemia in this study), the BBI supplemented mice appeared healthier in that they had shinier coats, had no radiation-induced hair loss (See FIG. 1), and weighed more than the non-BBI supplemented mice. Thus, the mice on the BBI-supplemented diet appeared to be a healthier population compared to those not on the BBI supplemented diet.

In other studies, the effect of BBI oral administration on cutaneous effects of radiation will be evaluated. Skin changes and hair loss will be observed in two groups of animals; C57BL mice exposed to whole body irradiation (WBI) and Sprague-Dawley rats following WBI.

To evaluate whether oral supplementation of BBI minimizes weight loss due to radiation, two groups of animals will be studied: C57BL mice exposed to WBI and Sprague-Dawley rats following WBI. Weight loss and food intake with and without addition of BBI will be serially monitored.

The invention is further illustrated by the following, nonlimiting examples.

EXAMPLES

Example 1

C57BL and CD-1 mice and Sprague Dawley rats are used in the studies. The experimental groups are as follows:
C57BL mice and Sprague Dawley rats:
WBI/gavage with 0.5% BBIC
WBI/gavage with 0.5% autoclaved BBIC
No treatment
Sham WBI/gavage with water
Gavage with 0.5% BBIC Upon arrival in the laboratory, the animals will be randomly assorted into treatment groups, housed 1-2 animals per cage and placed on a standard diet, AIN-76A. American Institute of Nutrition purified diets for rats and mice containing 20% protein. The BBIC will be administered 5 days per week via gavage. The BBIC will be prepared as described in the following Examples. Control animals will receive autoclaved BBI; autoclaving is believed to eliminate all protease inhibitor activity. The groups receiving the autoclaved BBIC preparation will serve as isocaloric diet control groups for other animals in the study. Animals will receive water ad libitum and will be maintained in a controlled environmental animal facility at 25° C. with a 12 hour light-dark cycle.

The C57BL mice and Sprague-Dawley rats will be maintained for 6 months following the end of the radiation treatments. Endpoints which are measured include visual skin and hair changes, body weight, food intake (to assure that any observed weight loss/gain is not due to differences in intake), progressive dermal biopsies and photographic appearance. At the time of autopsy, animals and individual organs will be weighed. The pancreas will be prepared for histopathological examination. It is important to evaluate the histopathological alterations in the pancreas because high levels of soybean protease inhibitors in rats have previously been associated with abnormal growth in the pancreas. However, in our studies, pancreatic histopathological alterations have not been observed in rats, hamsters, or mice utilizing BBI as a cancer preventative agent.

Example 2

Hair and weight loss in patients exposed to cancer therapy protocols utilizing radiation and/or chemotherapeutic agents will also be monitored. Many of the agents used in cancer therapy are known to produce hair and, presumably, weight loss. Patients treated for various malignancies with agents expected to produce hair and weight loss will be given pills containing BBIC or a placebo (to be taken on a daily basis). The endpoints to be monitored in the patients will include weight and any visual skin and hair changes, with photographic documentation. Patients will be observed over a 6-week period during and after receiving radiation and/or chemotherapy treatments.

Example 3

139 pounds of soybean solubles from an acidic aqueous extraction of hexane-defatted soybeans was diluted to 18% solids with 332 pounds of water. The slurry of the diluted soy solubles was centrifuged to remove insoluble matter, and the partially "purified" solids were further diluted with water to a 8% solids level. These "purified" soy solubles were then subjected to ultrafiltration using a 1,000 MW cut-off membrane at 15 gpm and 105 psig, until 31 gallons of permeate was collected. The liquid containing the crude BBI concentrate was again diluted with 31 gallons of water, and the ultrafiltration step was repeated until an additional 47 gallons of permeate was collected and 45 gallons of a semi-crude BBI concentrate remained.

At this point, 55 gallons of acetone was added to 25 gallons of the concentrate; the BBI concentrate precipitate thus obtained was allowed to settle for 1 hour. The liquid supernatant was then decanted, and the precipitate containing the "purified" BBI concentrate was placed in a Buchner Funnel under vacuum to draw off the excess liquid. The dried precipitate was ground in a Waring blender and reslurried to 15% solids. The reslurried suspension was then allowed to settle and the supernatant was lyophilized. The yield was 8 pounds of product with a Chymotrypsin inhibitor (CI) level of 135.5 mgs/g.

Example 4

87.3 pounds of soybean solubles from an acidic aqueous extraction of hexane-defatted soybeans were diluted to 18% solids with 207.5 pounds of water. The slurry was centrifuged to remove the insoluble sludge material; diluted to 8% solids with water; and then subjected to ultrafiltration over a 1,000 M cutoff membrane at 15 gpm. and 100 psig. 44 pounds of permeate was collected; the crude BBI concentrate was rediluted with 44 pounds of water, and the ultrafiltration step was repeated. 112 pounds of permeate and 163 pounds of a semicrude BBI concentrate were collected.

270 pounds of acetone was then added to this semi-crude BBI concentrate, and the precipitated BBI concentrate thus formed was allowed to settle for 1 hour. The liquid was decanted and the precipitate was placed in a Buchner funnel under vacuum to draw off the excess liquid. It was then reslurried with water in a Waring blender, allowed to settle, and the supernatant was spray-dried. The yield was 2.3 pounds of product with a Chymotrypsin (CI) content of 261 mgs/g.

Example 5

90 pounds of soybean solubles from an acidic aqueous extraction of hexane-defatted soybeans were diluted to between 15% to 20% of solids with water. (The initial solubles contain 50–60% solids). The slurry was centrifuged to remove 3–5% of the solids, present as insoluble sludge. The supernatant solution was then diluted with water to 10% solids, and subjected to ultrafiltration over a 1,000 MW cut-off membrane. One (1) pound of high-purity water was added to this fraction containing the crude BBI concentrate for every one (1) pound of permeate that had been removed. The ultrafiltration was considered complete when the solids content had begun to decrease. At that point, the BBI concentrate was spray-dried. The yield was 14 pounds of product with a CI content of 99.2 mgs/g.

Example 6

50.2 pounds of soybean solubles from an acidic aqueous extraction of hexane-defatted soybeans was diluted to 16% of solids with 126.2 pounds of water. The slurry was centrifuged to remove 3-5% of the solids, present as insoluble sludge. The supernatant solution was then diluted with water to 10% solids, and subjected to ultra-filtration over a 10,000 MW cut-off membrane. One (1) pound of high-purity water was added to the concentrate fraction for every one (1) pound of permeate that had been removed. When the solids content had begun to decrease in the permeate, the permeate was also subjected to ultrafiltration over a 1,000 MW cut-off membrane. After that, the BBI concentrate was spray-dried. The yield was 2.6 pounds of product with a CI content of 61.9 mgs/g.

Example 7

A slurry obtained from the whey protein stream produced during the production of soy protein isolate was treated by ultra filtration over a 1,000 MW cut-off membrane, as described in Example 4. A total of 157.75 pounds of whey protein solution was used. After ultra-filtration, the BBI concentrate fraction, containing 2.7% solids, was spray-dried. The yield was 1.2 pounds of product, containing 187.8 mgs/g of CI.

Example 8

1000 grams of soy solubles with a solids content of 19% from an acidic aqueous extraction of hexane-defatted soybeans were centrifuged to remove insoluble matter. At this point, 2 liters of acetone were added to the supernatant. The crude BBI concentrate precipitate thus obtained was allowed to settle for 1 hour. The liquid supernatant was then decanted. The precipitate containing the partially purified BBI was then resuspended in 200 ml of water and centrifuged to remove matter rendered irreversibly insoluble by acetone. 400 ml of acetone was then added to the supernatant. The water soluble, acetone insoluble precipitate which was formed was allowed to settle for 1 hour. The supernatant was decanted. The major portion of water remaining in the precipitate was removed by resuspending the precipitate in 100 ml of acetone and allowing the precipitate to settle for 30 minutes. The supernatant was decanted. The BBI concentrate precipitate was spread thinly on a tray and allowed to air dry to a free flowing white powder. The yield was 5 gm of product with a chymotrypsin inhibitor level of 200 mgs/g.

What is claimed is:

1. A method for inhibiting radiation induced weight and hair loss in an animal receiving radiation treatment comprising administering an effective amount of a Bowman Birk Inhibitor product wherein the Bowman Birk Inhibitor product is produced by the steps consisting essentially of:

(i) providing soybean solubles produced from acidic aqueous-extracted hexane-defatted soybeans;
(ii) diluting the soybean solubles with an aqueous solution to form a slurry;
(iii) separating the aqueous soluble portion of the soybean solubles from the slurry to form a purified soybean soluble composition;
(iv) diluting the purified soybean soluble composition with an aqueous solution and ultrafiltering the aqueous soluble portion of the diluted purified soybean soluble composition at least once to form a crude Bowman-Birk Inhibitor concentrate; and
(v) drying the crude Bowman-Birk Inhibitor concentrate to produce a Bowman-Birk Inhibitor concentrate product; to said animal.

2. The method of claim 1 wherein said administration is oral.

3. The method of claim 1 wherein the drying method used in step (v) is spray drying.

4. The method of claim 1 wherein the slurry of step (ii) is a 15 to 20 percent solid solution.

5. The method of claim 1 further comprising diluting the crude Bowman-Birk Inhibitor concentrate produced in step (iv) with an aqueous solution and separating a semi-crude Bowman Birk Inhibitor concentrate prior to drying in step (v).

6. The method of claim 5 further comprising, prior to the drying step, diluting the semi-crude Bowman-Birk Inhibitor concentrate with acetone and retaining the precipitated acetone insoluble portion.

7. The method of claim 6 further comprising lyophilizing the dried Bowman-Birk Inhibitor product.

8. A method for inhibiting radiation induced weight and hair loss in an animal receiving radiation treatment comprising administering an effective amount of a Bowman Birk Inhibitor product wherein the Bowman Birk Inhibitor product is produced by the steps consisting essentially of:

(i) providing soybean solubles from acidic aqueous-extracted hexane-defatted soybeans;
(ii) diluting the soybean solubles with water and separating a first aqueous soybean soluble portion;
(iii) adding acetone to the first aqueous portion to produce a first Bowman-Birk Inhibitor precipitate concentrate;
(iv) diluting the first concentrate with water and separating a second aqueous soybean soluble portion;
(v) adding acetone to the second aqueous portion to produce a second Bowman-Birk Inhibitor precipitate concentrate;
(vi) drying the second Bowman-Birk Inhibitor concentrate to produce a Bowman-Birk Inhibitor concentrate product; to said animal.

9. The method of claim 8 wherein the drying step is spray drying.

10. The method of claim 9 further comprising adding acetone to the second Bowman Birk Inhibitor concentrate prior to the drying step.

11. The method of claim 10 further comprising lyophilizing the dried Bowman Birk Inhibitor concentrate product.

* * * * *